United States Patent
Chowdhury et al.

(10) Patent No.: US 12,013,115 B2
(45) Date of Patent: Jun. 18, 2024

(54) COMBUSTION SYSTEM

(71) Applicant: Indian Institute of Technology Bombay, Mumbai (IN)

(72) Inventors: Arindrajit Chowdhury, Mumbai (IN); Abhishek Gupta, Mumbai (IN); Ashtesh Kumar, Mumbai (IN)

(73) Assignee: INDIAN INSTITUTE OF TECHNOLOGY, Bombay /Maharashtra (IN)

( * ) Notice: Subject to any disclaimer, the term of this patent is extended or adjusted under 35 U.S.C. 154(b) by 444 days.

(21) Appl. No.: 17/266,035

(22) PCT Filed: Sep. 23, 2019

(86) PCT No.: PCT/IN2019/050694
§ 371 (c)(1),
(2) Date: Feb. 4, 2021

(87) PCT Pub. No.: WO2020/065665
PCT Pub. Date: Apr. 2, 2020

(65) Prior Publication Data
US 2021/0310649 A1 Oct. 7, 2021

(30) Foreign Application Priority Data
Sep. 24, 2018 (IN) .............................. 201821035841

(51) Int. Cl.
| | |
|---|---|
| F23C 13/08 | (2006.01) |
| B01J 23/34 | (2006.01) |
| F02P 19/02 | (2006.01) |
| F23C 13/02 | (2006.01) |

(52) U.S. Cl.
CPC .............. *F23C 13/08* (2013.01); *F23C 13/02* (2013.01); *B01J 23/34* (2013.01); *F02P 19/026* (2013.01)

(58) Field of Classification Search
CPC ............ F23C 13/08; F23C 13/02; B01J 23/34
USPC .......................................... 431/12
See application file for complete search history.

(56) References Cited

U.S. PATENT DOCUMENTS

| | | | | |
|---|---|---|---|---|
| 4,385,489 A | * | 5/1983 | Abbott ...................... | F02K 9/50 60/776 |
| 2020/0197899 A1 | * | 6/2020 | Roy ........................ | B01J 16/005 |

OTHER PUBLICATIONS

Zope, Mandar., Chowdhury, Arindrajit., Gupta, Abishek. "Modeling and control for a monopropellant-powered actuator".2014 IEEE/ASME International Conference on Advanced Intelligent Mechatronics. 2014 (Year: 2014).*

* cited by examiner

*Primary Examiner* — Vivek K Shirsat

(57) ABSTRACT

Embodiments herein provide a combustion system comprising a combustion chamber having a catalyst bed, and a vessel for storing a propellant at a predefined pressure. The vessel comprising a first valve for controlling a flow of the propellant over the catalyst bed inside the combustion chamber and an input provided at the first valve, for injecting the propellant inside the combustion chamber at a predefined duration of injection for each cycle of injection. A predefined quantity of the propellant is injected in each cycle of the injection. The combustion system further comprises one or more glow plugs for maintaining a predefined temperature within the catalyst bed and an ignition glow plug for providing a source of ignition for combustion of the propellant inside the combustion chamber.

14 Claims, 7 Drawing Sheets

COMBUSTION SYSTEM

FIELD OF INVENTION

Present disclosure in general, relates to combustion process and more particularly to combustion systems. The present application is based on, and claims priority from International application number PCT/IN2019/050694 filed on 23 Sep. 2019 and an Indian Application Number 201821035841 filed on 24 Sep. 2018, the disclosure of which is hereby incorporated by reference herein.

BACKGROUND OF INVENTION

With mobile automation, large number of power resources have been developed. In past few years, lot of research has been carried out with regard to development of alternate power resources.

Among plausible power sources for many application areas such as under water and space, direct current (DC) power supplies generate long-lasting power output at cost of energy density. Whereas, liquid fuel-powered sources are plagued by a prohibitively high requirements for oxidizers in anaerobic environments.

Existing power supplies are mainly battery based and are plagued with low energy densities i.e. to provide same energy more mass is required to be carried on the operating vehicle. The existing fuel-based power system are heavily dependent on atmospheric compositions for oxygen, hence may not be used in places like extra-terrestrial planets devoid of oxygen Monopropellants, such as hydrazine and hydrogen peroxide, are compounds that decompose exothermically though one of catalytic modes or through thermal modes to generate gases. The gases may be expanded pneumatically to extract generated energy. Hence, such monopropellants may be utilized in such environments as a potential power source. However, development of highly efficient combustion system supporting combustion of the monopropellants in an economic way still remains a challenge.

OBJECT OF INVENTION

The principal object of the embodiments herein is to provide a combustion system.

Another object of the embodiments herein is to provide the combustion system with a combustion chamber facilitating combustion.

SUMMARY

Accordingly, embodiments herein provide a combustion system comprising a combustion chamber having a catalyst bed, and a vessel for storing a propellant at a predefined pressure. The vessel comprising a first valve for controlling a flow of the propellant over the catalyst bed inside the combustion chamber; and an input provided at the first valve, for injecting the propellant inside the combustion chamber at a predefined duration of injection for each cycle of injection. A predefined quantity of the propellant is injected in each cycle of the injection. The combustion system further comprises one or more glow plugs for maintaining a predefined temperature within the catalyst bed and an ignition glow plug for providing a source of ignition for combustion of the propellant inside the combustion chamber.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF FIGURES

This combustion system is illustrated in the accompanying drawings, throughout which like reference letters indicate corresponding parts in the various figures. The embodiments herein will be better understood from the following description with reference to the drawings, in which.

DETAILED DESCRIPTION OF INVENTION

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. Also, the various embodiments described herein are not necessarily mutually exclusive, as some embodiments can be combined with one or more other embodiments to form new embodiments. The term "or" as used herein, refers to a non-exclusive or, unless otherwise indicated. The examples used herein are intended merely to facilitate an understanding of ways in which the embodiments herein can be practiced and to further enable those skilled in the art to practice the embodiments herein. Accordingly, the examples should not be construed as limiting the scope of the embodiments herein.

Accordingly, embodiments herein provide a combustion system with a combustion chamber supporting a decomposition of propellant (mixture of 50% $H_2O_2$), with a catalyst being chosen as $MnO_2$. The combustion system is disclosed to determine decomposition characteristics of $H_2O_2$ and to verify a viability of the combustion system as a possible energy source for a pneumatic actuator. The combustion system may also be equipped to handle a combustion of 50% $H_2O_2$ with a suitable miscible hydrocarbon or alcohol. The combustion system also predicts a behavior of combustion chamber in the combustion system and aids a development of a control algorithm capable of controlling an exhaust pressure to pre-determined values by modulating a solenoid valve controlling an injection of propellant. The system was determined to be a successful step towards developing high-energy-density power sources.

Proposed combustion system may provide actuations in anaerobic environments and may develop a combustion system with high reliability and repeatability in terms of performance.

Figure 1:
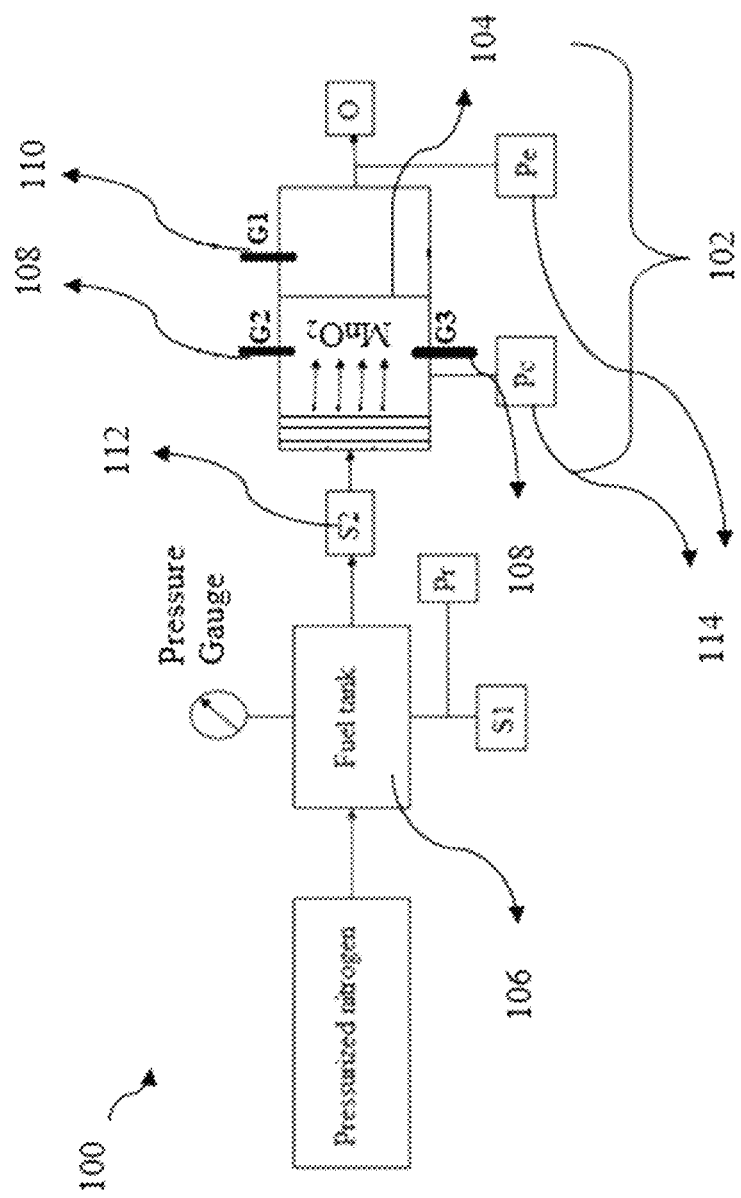
FIG. 1 illustrates a combustion system, according to the embodiments as disclosed herein.

In accordance with an embodiment, referring to FIG. 1, a combustion system 100 is shown. The combustion system 100 comprises a combustion chamber 102 with a catalyst bed 104, a vessel 106 (also referred as fuel vessel or propellant vessel) for storing propellant, one or more glow plugs 108 (shown as G2 and G3) and an ignition glow plug 110 (shown as G1). The vessel 106 comprises a first valve 112 (referred as S2 for controlling the input of the propellant into the combustion chamber 102 to measure the pressure inside the combustion chamber 102). Valve S1 is configured for releasing the pressure in the vessel 106 (also referred as fuel tank).

Figure 2:
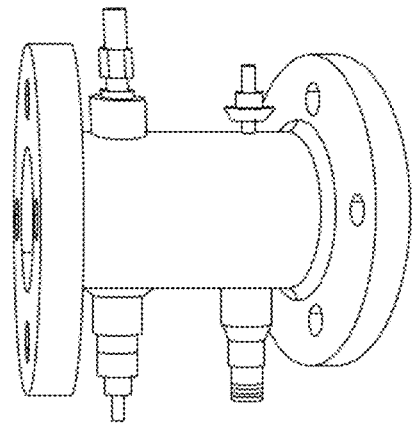
FIG. 2 illustrates details of combustion chamber of the combustion system of FIG. 1, according to the embodiments as disclosed herein.
Figure 2:
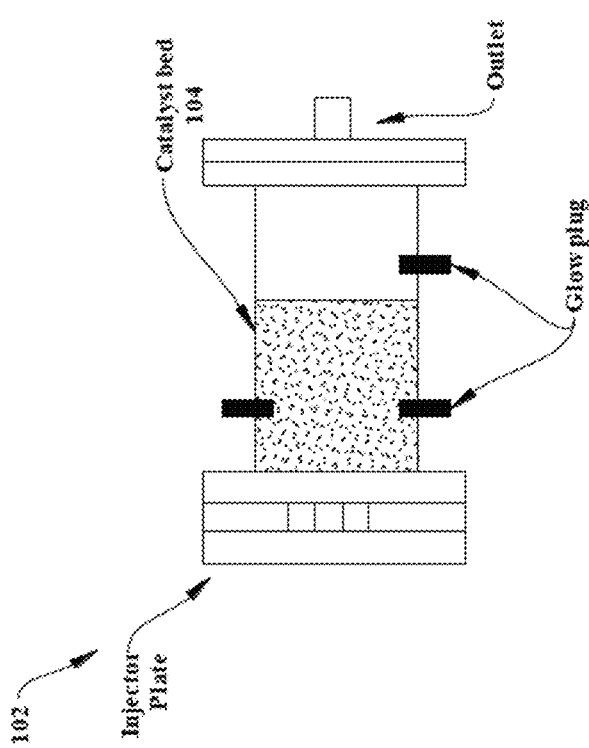

Details of the combustion system 100 will now be explained. Referring to FIG. 2, the combustion chamber 102 is shown. The combustion chamber 102 is provided with the catalyst bed 104 having a catalyst. The catalyst in the catalyst bed 104 comprises of $MnO_2$ with a mean particle diameter in a range of 2 mm to 5 mm. The catalyst bed 104 is selected with a predefined width. The predefined width comprises in a range of 35 mm to 45 mm.

For applications like robotic actuations in accessible places where the catalyst can be replenished at regular intervals, $MnO_2$ is a viable option for catalyst. $MnO_2$ was found to sustain the high temperatures inside the combustion chamber for up-to 300 s after which the exhausted catalyst has to be replaced with new active catalyst. Specific diameter of the catalyst particles and bed 104 is selected so as to provide enough porosity in catalyst bed to facilitate low pressure drop across the catalyst bed 104 and a desired residence time for the ignitable mixture (fuel mixture) to react. In an example embodiment, the diameter of the catalyst bed 104 may be selected in range of 35 mm to 45 mm and the length may be selected in a range of 55 mm to 65 mm. The dimensions of the catalyst bed 104 (each of the length and the diameter) primarily depends on a flow rate to be faced by the combustion chamber 102.

In an example, the flow rate comprises in a range of 20 gm/s to gm/s. Configuration of the catalyst bed 104 with respect to a position of the injector plate is shown in FIG. 2 (details of injector discussed later). The catalyst particle may be retained in the combustion chamber 102 through a wire mesh attached at the end of the catalyst bed 104. At least two glow plugs 108 were also attached to heat the catalyst bed 104 (details of the at least two glow plugs 108 are discussed later).

Dimensions of the catalyst bed 104 are preselected. Each of length of the catalyst bed 104 and diameter of the catalyst bed 104 are preselected. A ratio of length to diameter (L/D) of the catalyst bed 104 is important as diameter of the catalyst bed 104 determines a maximum flow rate of monopropellant the catalyst may be able to decompose, and the length of the catalyst bed 104 determines a residence time of the propellant (monopropellant) into the combustion chamber 102 further determining a combustion efficiency of the combustion system 100.

The combustion chamber 102 may be operated in pulse mode at a frequency in range of 1 Hz to 2 Hz and duty cycle in a range of 70 ms to 85 ms (every 1 second the fuel may be injected in a range of 70 ms to 85 ms), to prevent flooding of the combustion chamber 102 because of diluted hydrogen peroxide. The operation as discussed above, provides more surface area to the propellant (fuel mixture) injected on the catalyst bed 104 for efficient decomposition.

The combustion takes place inside the combustion chamber 102 in presence of water in the propellant and is beneficial to the combustion system 100 as water decreases the combustion temperature and thereby increases the life of catalyst. The propellant is injected inside the combustion chamber 102 in pulses to avoid a loss of the catalyst or to prevent flooding and reduction in decomposition/combustion efficiency.

The vessel 106 in the combustion system 100 is configured for storing the propellant at a predefined pressure. The vessel 106 comprises of a stainless-steel pressure vessel. The predefined pressure comprises in a range of 8 bar to 15 bar.

The propellant comprises one of a $H_2O_2$ in a preselected percentage. The predefined percentage comprises in a range of 50% to 90%. The propellant also comprises one of a methanol, ethanol, or propanol in presence of water. The propellant is stored inside the vessel 106 and pressurized by using an inert gas. The inert gas comprises one of a nitrogen.

The vessel 106 further comprises the first valve 112 for controlling a flow of the propellant over the catalyst bed 104 inside the combustion chamber 102. The combustion chamber 102 is provided with a shower head injector for enabling a uniform distribution of the propellant on surface of the catalyst bed 104. The injector is designed so as to maximize the penetration of propellant into the catalyst bed. The combustion chamber 102 comprises the solenoid valve (S2 the first valve 102) and the injector comprises a high pressure drop shower head injector which imparts high axial velocity to the propellant.

Figure 3:
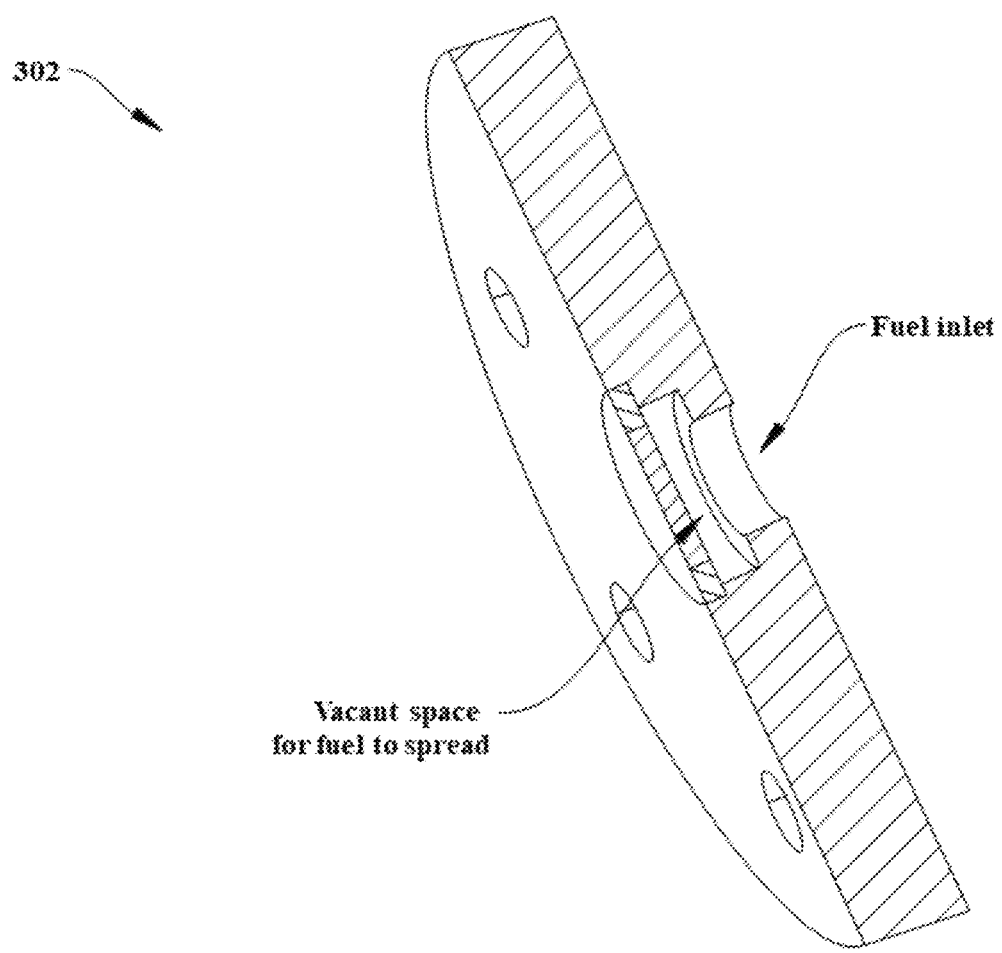
FIG. 3 illustrates details of injector of provided in catalyst bed of the combustion system, according to the embodiments as disclosed herein.

Referring to FIG. 3, the shower head injector 302 is shown. The shower head injector 302 spreads the propellant (mixture of propellants) uniformly on to the catalyst bed 104. To achieve this, a predefined number of holes (with each hole of diameter in a range of 0.4 mm to 0.8 mm) may be drilled on a 5 mm thick stainless-steel plate using electro discharge machining (EDM). The predefined number of holes comprise four holes drilled at PCD (pitch circle diameter) in a range of 16 mm to 25 mm to create the uniform spread of the fuel on the catalyst bed 104.

The vessel 106 further comprises an input provided at the first valve 112, for injecting the propellant inside the combustion chamber 102 at a predefined duration of injection for each cycle of injection. Fuel is injected in a predefined quantity in each cycle of the injection. Each injection cycle comprises a predefined number of injection cycles. The predefined number of injection cycles comprise in a range of 80 injection cycles to 130 injection cycles by pushing the first valve at a frequency of 1 Hz in a range of 15% to 30% on-time. The predefined duration of injection comprises in a range of 50 ms to 100 ms, and the predefined quantity of the propellant comprises in a range of 5 gm to 6 gm. The number of cycles may be increased upon using catalyst of higher structural integrity The combustion chamber 102 further comprises one or more glow plugs 108 for maintaining a predefined temperature of ignition source within the catalyst bed 104. The predefined temperature of the ignition source comprises in a range of 600 K to 700 K. In an example, the one or more glow plugs 108 comprises at least two glow plugs (G2 and G3). External heaters to heat the catalyst bed 104 to auto-ignition temperature of fuel can also be used to produce the same effect.

The combustion chamber 102 further comprises an ignition glow plug (second glow plug) 110 for providing a source of ignition for combustion of the propellant inside the combustion chamber 102. The ignition glow plug 110 is provided in the gas phase between the injector 302 and the catalyst bed 104.

Each of the one or more glow plugs 108 and the ignition glow plug 110 are powered by a 12 DC power supply.

Again, referring to FIG. 1, the combustion system 100 further comprises at least two pressure transducers (P, and P e) 114 mounted on the combustion chamber 102 and an exhaust line for monitoring a variation of pressure with respect to time. The at least two pressure transducers 114 are protected by a column of silicon-based oil to prevent a contact of high temperature corrosive gases with piezoelectric sensors. The at least two pressure transducers 114 may be powered by 24V DC power supply.

A unidirectional flow control valve (V1) was provided before the injector 302 to prevent the backflow of hot gases from the combustion chamber 102 to the vessel (fuel tank) 106.

The combustion system 100 further comprises a unidirectional flow control valve for preventing a backflow of hot gases form the combustion chamber 102 to the vessel 106.

As part of combustion process performed by the combustion system 100, $H_2O_2$ is decomposed to generate steam and oxygen, ethanol in presence of oxygen and ignition glow plug 110 combusts to give high temperature gases.

Combustion data may be acquired through a data acquisition system at the rate of 1000 Hz for future processing and research.

Figure 4:
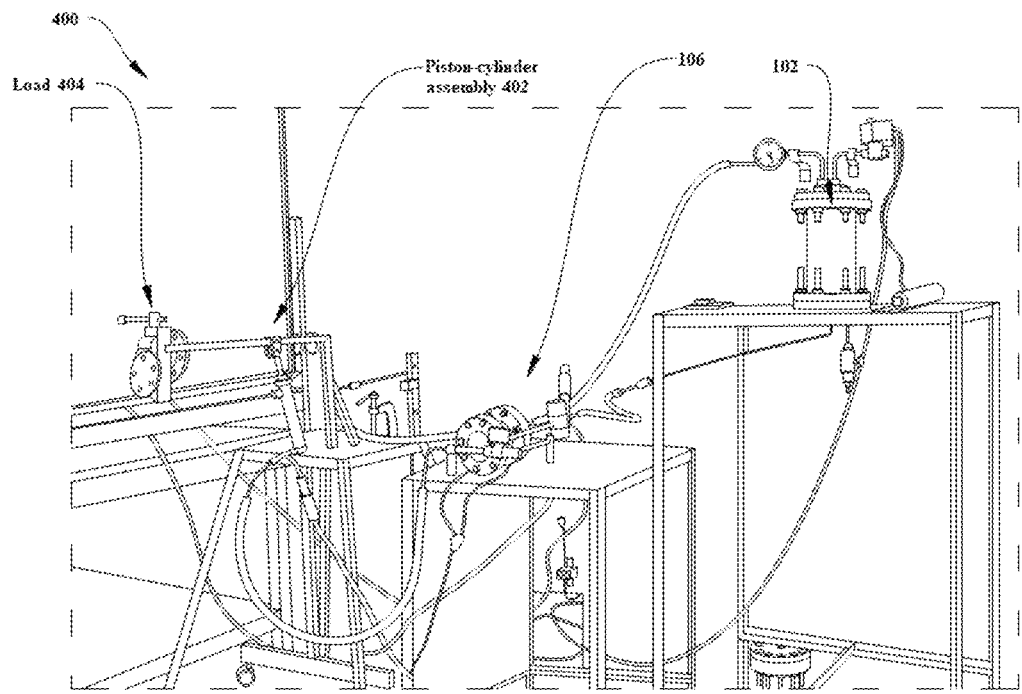
FIG. 4 illustrates an experimental setup demonstrating an operation of the combustion system of FIG. 1, according to the embodiments as disclosed herein.

In an example embodiment, referring to FIG. 4, an experimental set-up 400 of the combustion system 100 is shown. Before the injection of the fuel into the combustion chamber 102, the at least glow plugs 108 may be turned on for three minutes to heat the catalyst bed 104 and internal environment of the combustion chamber 102 to a uniform temperature. The presence of the at least glow plugs 108 may produce locally hot zones within the catalyst bed 102, to promote catalytic decomposition of $H_2O_2$. The experimental set-up shows the piston-cylinder assembly 402 connected to the combustion chamber 102 and the load 404 connected to the piston-cylinder assembly 402.

While the decomposition of $H_2O_2$ may proceed without the at least glow plugs 108 within the catalyst bed 104, the combustion process is strongly temperature-dependent, and a decomposition rate of fuel increases exponentially with temperature. Thus, the at least two glow plugs 108 within the catalyst bed 104 ensure rapid decomposition of $H_2O_2$. Upon injection, as $H_2O_2$ comes in contact with the $MnO_2$ particles, and the $H_2O_2$ decomposes into steam and reactive oxygen (referred as hot gases). The hot gases may be allowed to escape from the combustion chamber 102 to the atmosphere either through an orifice plate or to the piston cylinder assembly 402 attached to the load 404 of around 10 kg as shown in FIG. 4. The hot gases may exert a force on the piston cylinder assembly 402 so as to produce a linear motion thus producing work.

In the example of FIG. 4, the monopropellant may be selected for combustion. The monopropellant comprises in a combination of 45% $H_2O_2$, 45% $H_2O$ and 10% ethanol (referred as mixture) chosen to be burnt in the combustion chamber. The energy density of the mixture is 4.12 MJ/kg. The mixture is diluted with 45% water to reduce the temperatures faced by the catalyst, ensuring a longer life time of the catalyst bed 106.

Figure 5:
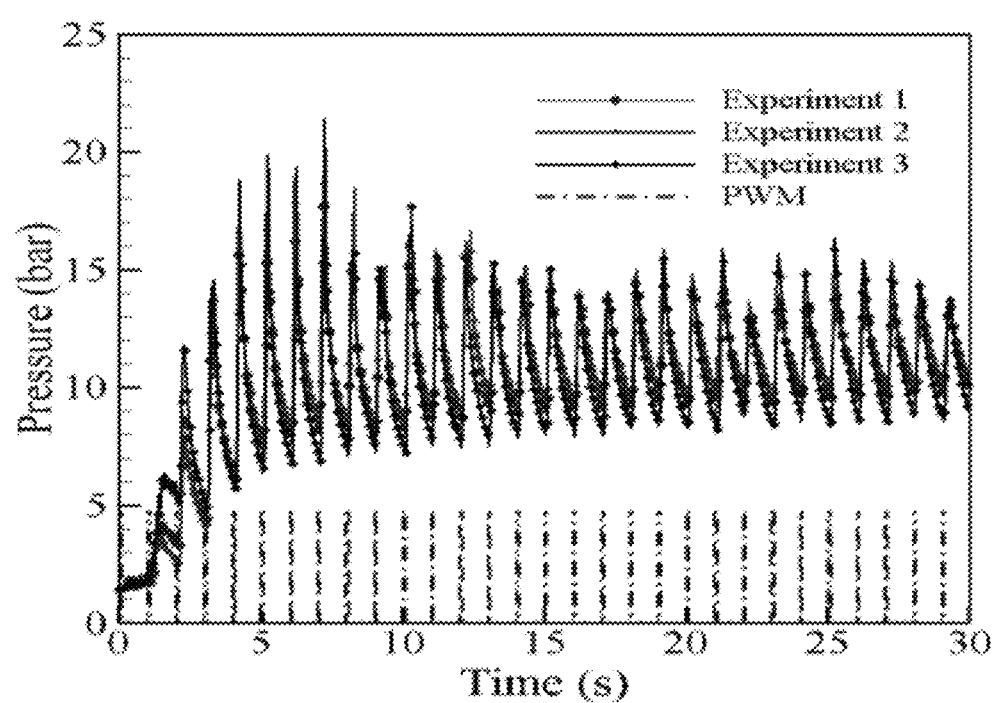
FIG. 5 shows graphical illustration of Pressure trace inside the combustion chamber during operation, according to the embodiments as disclosed herein.
Figure 6:
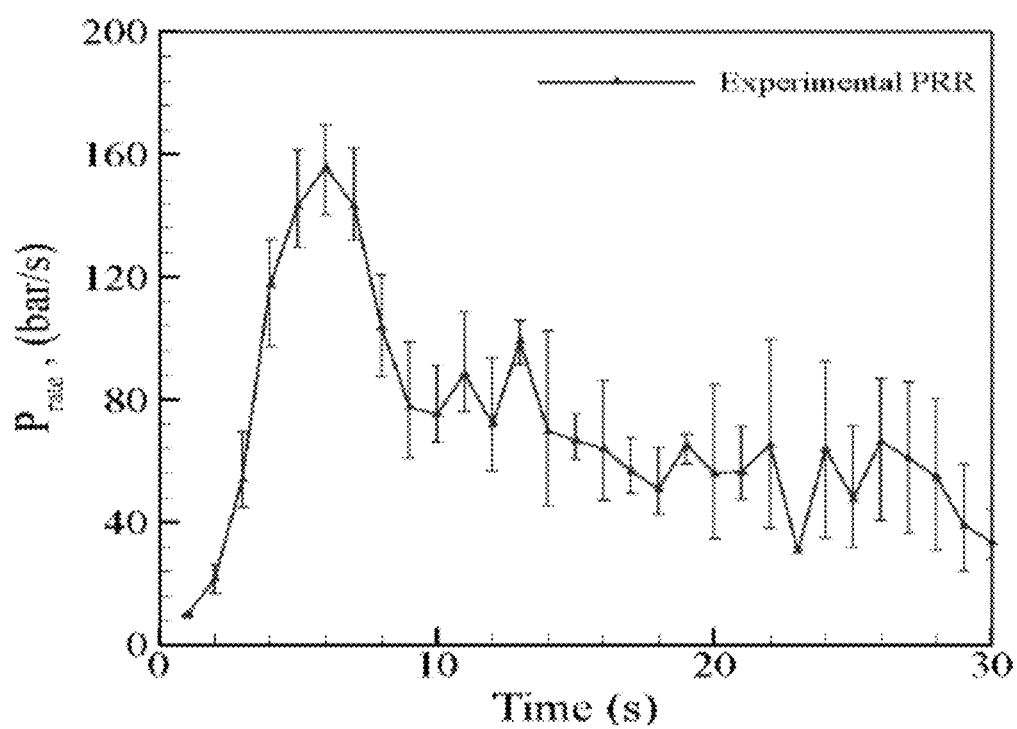
FIG. 6 shows graphical illustration of pressure rise rates during operation, according to the embodiments as disclosed herein.
Figure 7:
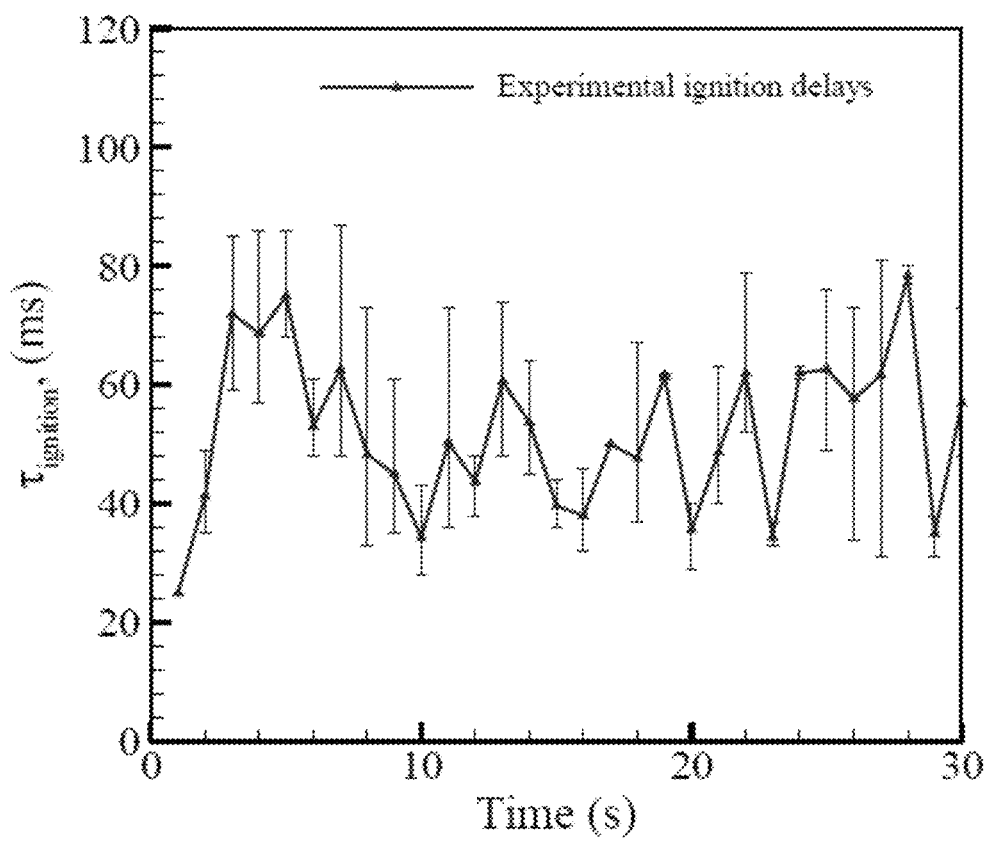
FIG. 7 shows graphical illustration of ignition delay during operation, according to the embodiments as disclosed herein.

Referring to FIG. 5, FIG. 6 and FIG. 7 in combination, the pressure in the combustion chamber 102 may be recorded for calculating one or more combustion characteristics. The one or more combustion characteristics comprises an ignition delay and pressure rise rates may be calculated for evaluating a performance of the combustion chamber. Pressure rise rates in a range of to 140 bar/s to 150 bar/s and ignition delay lower than 80 ms may be obtained in the combustion chamber.

FIG. 5 shows graphical illustration of pressure trace inside the combustion chamber during operation.

FIG. 6 shows graphical illustration of pressure rise rates during operation.

FIG. 7 shows graphical illustration of ignition delay during operation.

The proposed combustion system 100 provides a combination of high energy density system along with independence of performance on atmospheric composition. Each of the fuel and oxidizer are premixed hence only single storage and delivery system are required in the combustion system 100 hence cutting down the weight as compared to conventional power systems. Exhaust of the combustion system 100 comprises of each of carbon dioxide and water vapor as ethanol burns with a clean flame, hence the combination is environmentally benign and the monopropellant is often referred to as green fuel. The density of the monopropellant is higher than conventional fuels, hence the combustion system 100 has lower requirement of volume for the same amount of work output, hence making the combustion system 100 is highly compact. The combustion system 100 is cheap and comprises easily replaceable $MnO_2$ catalyst bed unit and may be refilled after completion of lifetime of the catalyst bed. Higher specific fuel consumption per unit power may be produced due to controllable fuel input frequency as compared to continuous gas generation system.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

What is claimed:

1. A combustion system (100), comprising:
    a combustion chamber (102) having a catalyst bed (104);
    a vessel (106) for storing a propellant at a predefined pressure, the vessel (106) comprises:
        a first valve (112) for controlling a flow of the propellant over the catalyst bed (104) inside the combustion chamber (102); and
        a shower head injector (302) provided at the first valve (112), for injecting the propellant inside the combustion chamber (102), at a predefined duration of injection for each cycle of injection, wherein a predefined quantity of the propellant is injected in each cycle of the injection;

the shower head injector (302) provided at the first valve (112) for enabling a uniform distribution of the propellant on the catalyst bed (104), wherein the shower injector is placed adjacent to the catalyst bed (104) such that such that there is no propellant accumulation zone between the shower head injector (302) and the catalyst bed (104);

one or more glow plugs (108) for maintaining a predefined temperature within the catalyst bed (104); and an ignition glow plug (110) for providing a source of ignition for combustion of the fuel solution inside the combustion chamber (102), wherein the predefined duration of injection comprises a range of 70 ms to 85 ms, and wherein the predefined quantity of propellant comprises a range of 5 gm to 6 gm per injection cycle and the injector has 4 holes distributed uniformly on a PCD (pitch circle diameter) of 16 mm to 25 mm or 45% to 55% of the diameter of catalyst bed (104) for uniform distribution of the propellant on surface of the catalyst bed (104).

2. The combustion system (100) as claimed in claim 1, wherein the propellant comprises $H_2O_2$ in a predefined percentage and one of a methanol, ethanol or propanol in presence of water, wherein the predefined percentage comprises a range of 50% to 90%.

3. The combustion system (100) as claimed in claim 1, wherein the vessel (106) comprises a stainless-steel pressure vessel, and wherein the predefined pressure comprises a range of 8 bar to 15 bar.

4. The combustion system (100) as claimed in claim 1, wherein the propellant is stored inside the vessel (106) pressurized by using an inert gas, wherein the inert gas comprises nitrogen.

5. The combustion system (100) as claimed in claim 1, wherein the catalyst length is chosen to be 1.2 to 1.8 times the diameter of the catalyst bed (104).

6. The combustion system (100) as claimed in claim 1, wherein catalyst in the catalyst bed (104) comprises manganese dioxide with a mean particle diameter a range of 2 mm to 5 mm for optimizing the pressure drop across the catalyst bed (104).

7. The combustion system (100) as claimed in claim 1, wherein each injection cycle comprises a predefined number of injection cycles, wherein the predefined number of injection cycles comprise a range of 80 injection cycles to 130 injection cycles for $MnO_2$ catalyst.

8. The combustion system (100) as claimed in claim 1, wherein the predefined temperature of ignition source comprises a range of 600 K to 700 K.

9. The combustion system (100) as claimed in claim 1, wherein the injector has 4 holes of the size of 0.4 mm to 0.8 mm which imparts high axial velocity to increase the penetration of propellant into the catalyst bed (104).

10. The combustion system (100) as claimed in claim 1, comprises:
a unidirectional flow control valve for preventing a backflow of hot gases form the combustion chamber (102) to the fuel tank.

11. The combustion system (100) as claimed in claim 1, wherein the ignition glow plug (110) is provided in a gas phase between the exhaust and the catalyst bed (104) to ignite the gases coining from catalyst bed (104).

12. The combustion system as claimed in claim 1, wherein the total catalyst length is chosen between 55 mm to 65 mm.

13. The combustion system as claimed in claim 1, wherein the frequency of propellant injection is 1 Hz to 2 Hz with duty cycle as low as 7% to 8.5%, to allow the catalyst bed enough time to decompose the propellant efficiently.

14. The combustion system as claimed in claim 1, wherein two heating glow plug is provided in the catalyst bed for uniform heating of the catalyst bed which increases the hydrogen peroxide decomposition rate.

* * * * *